US00PP33327P2

(12) United States Plant Patent
Ullrich

(10) Patent No.: US PP33,327 P2
(45) Date of Patent: Aug. 10, 2021

(54) ***ROSA* PLANT NAMED 'ESM R325'**

(50) Latin Name: *Rosa hybrida*
Varietal Denomination: ESM R325

(71) Applicant: Clarisse Ullrich, Quito (EC)

(72) Inventor: Clarisse Ullrich, Quito (EC)

(73) Assignee: TECHNOVIV LLC, Miami, FL (US)

( * ) Notice: Subject to any disclaimer, the term of this patent is extended or adjusted under 35 U.S.C. 154(b) by 0 days.

(21) Appl. No.: 16/945,786

(22) Filed: Jul. 31, 2020

(51) Int. Cl.
*A01H 5/02* (2018.01)
*A01H 6/74* (2018.01)

(52) U.S. Cl.
USPC ..... Plt./140
CPC ..... *A01H 6/749* (2018.05); *A01H 5/02* (2013.01)

(58) Field of Classification Search
USPC ..... Plt./140
CPC ..... A01H 6/749
See application file for complete search history.

*Primary Examiner* — Anne Marie Grunberg
(74) *Attorney, Agent, or Firm* — C. Anne Whealy

(57) ABSTRACT

A new and distinct cultivar of Rose plant named 'ESM R325', characterized by its upright and strong flowering stems; vigorous growth habit; dark green-colored leaves; thornless stems; red-colored flowers; and excellent postproduction longevity.

1 Drawing Sheet

Botanical designation: *Rosa hybrida.*
Cultivar denomination: 'ESM R325'.

CROSS-REFERENCED TO RELATED APPLICATIONS AND STATEMENT REGARDING PRIOR DISCLOSURES BY INVENTOR/APPLICANT AND ASSIGNEE

U.S. Plant Patent application:
Title: *Rosa* Plant Named 'ESM R394'
Inventor/Applicant: Clarisse Ullrich
Filed: Concurrently with the instant application having application Ser. No. 16/945,792
European Community Plant Breeders' Rights application:
Filed: Mar. 7, 2019
Application number: 2019/0611
Ecuadorian Plant Breeders' Rights application:
Filed: Apr. 24, 2019
Application number: 1597-19

There have been no offers for sale anywhere in the world prior to the effective filing date of this Application and no accessibility to one of ordinary skill in the art could have been derived from the printed Plant Breeder's Rights documents.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R325'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in August, 2013 of a proprietary Rose selection identified as Line R567, not patented, as the female, or seed, parent with a proprietary Rose selection identified as Line R770, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in October, 2014.

Asexual reproduction of the new Rose plant by bud grafting in El Quinche, Pichincha, Ecuador since November, 2014 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R325'. These characteristics in combination distinguish 'ESM R325' as a new and distinct Rose plant:

1. Upright and strong flowering stems.
2. Vigorous growth habit.
3. Dark green-colored leaves.

4. Thornless stems.
5. Red-colored flowers.
6. Excellent postproduction longevity.

Plants of the new Rose differ from plants of the female parent selection in the following characteristics:

1. Plants of the new Rose are more vigorous than plants of the female parent selection.
2. Stems of plants of the new Rose do not have thorns whereas stems of plants of the female parent selection have medium thorn density.
3. Flowers of plants of the new Rose have fewer petals than flowers of plants of the female parent selection.

Plants of the new Rose differ from plants of the male parent selection in the following characteristics:

1. Stems of plants of the new Rose do not have thorns whereas stems of plants of the male parent selection have medium thorn density.
2. Flowers of plants of the new Rose have fewer petals than flowers of plants of the male parent selection.
3. Flowers of plants of the new Rose are lighter red in color than flowers of plants of the male parent selection.

Plants of the new Rose can be compared to plants of *Rosa hybrida* 'ESM R394', disclosed in a U.S. Plant Patent application filed concurrently having application Ser. No. 16/945,792. Plants of the new Rose differ from plants of 'ESM R394' in the following characteristics:

1. Plants of the new Rose flower about eleven days later than plants of 'ESM R394'.
2. Plants of the new Rose have smaller flowers with fewer petals than plants of 'ESM R394'.
3. Plants of the new Rose have red-colored flowers whereas plants of 'ESM R394' have purplish pink-colored flowers.

Plants of the new Rose can also be compared to plants of *Rosa hybrida* 'ESM R068', disclosed in U.S. Plant Pat. No. 24,405. Plants of the new Rose differ from plants of 'ESM R068' in the following characteristics:

1. Plants of the new Rose are taller than plants of 'ESM R068'.
2. Stems of plants of the new Rose do not have thorns whereas stems of plants of 'ESM R068' have medium thorn density.
3. Plants of the new Rose have slightly smaller flowers than plants of 'ESM R068'.
4. Flowers of plants of the new Rose have fewer petals than flowers of plants of 'ESM R068'.

BRIEF DESCRIPTION OF THE PHOTOGRAPH

The accompanying colored photograph illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant. The photograph at the left of the sheet is a side perspective of a typical flowering stem of 'ESM R325'.

The photograph at the upper right of the sheet is a close-up view of a typical developed flower of 'ESM R325'.

The photographs at the lower right of the sheet are close-up views of the upper and lower surfaces of typical leaves of 'ESM R325'.

DETAILED BOTANICAL DESCRIPTION

The aforementioned photograph, following observations and measurements describe plants grown in 10-liter containers in a polyethylene-covered greenhouse in El Quinche, Pichincha, Ecuador and under typical hydroponic Rose production practices. Plants were pinched 14 weeks after planting and were 63 weeks old when the photograph and the description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2015 Edition, except where general terms of ordinary dictionary significance are used.

Botanical classification: *Rosa hybrida* 'ESM R325'.

Parentage:

*Female, or seed, parent*.—Proprietary seedling selection of *Rosa hybrida* identified Line R567, not patented.

*Male, or pollen, parent*.—Proprietary seedling selection of *Rosa hybrida* identified Line R770, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a standard type; vigorous growth habit and rapid growth rate.

*Productivity*.—Plants of the new Rose are highly productive with about 11.4 flowering stems developing per plant per year.

*Plant height*.—About 190 cm.

*Plant width* (*spread*).—About 54 cm.

*Lateral branches*.—Length: About 106 cm. Diameter: About 8.7 mm Internode length: About 5.5 cm. Texture and luster: Smooth, glabrous; matte. Strength: Strong. Color, developing: Close to N199A. Color, developed: Close to 146A. Thorns: To date, thorn development has not been observed on plants of the new Rose.

Leaf description:

*Arrangement*.—Alternate; compound with typically seven leaflets per leaf.

*Leaf length*.—About 18.9 cm.

*Leaf width*.—About 13.2 cm.

*Leaflet length*.—About 7.8 cm.

*Leaflet width*.—About 4.6 cm.

*Leaflet shape*.—Ovate.

*Leaflet apex*.—Acuminate.

*Leaflet base*.—Obtuse.

*Leaflet margin*.—Serrate.

*Leaflet texture and luster, upper surface*.—Smooth, glabrous; moderately glossy.

*Leaflet texture and luster, lower surface*.—Smooth, glabrous; matte.

*Leaflet venation pattern*.—Pinnate.

*Leaflet color*.—Developing leaflets, upper surface: Close to 139A. Developing leaflets, lower surface: Close to 147B. Fully expanded leaflets, upper surface: Close to 147A; venation, close to 147B. Fully expanded leaflets, lower surface: Close to 187A; venation, close to 146D.

*Petioles*.—Length: About 1.7 cm. Diameter: About 2.2 mm Strength: Strong. Texture and luster, upper surface: Glandular; matte. Texture and luster, lower surface: Smooth, glabrous; moderately glossy. Color, upper surface: Close to 181B, 146B and N77A. Color, lower surface: Close to 143A.

*Stipules*.—Arrangement and appearance: Two, adnate to the petiole, leafy in appearance. Length: About 2.4 cm. Width: About 2 mm Shape: Roughly deltoid. Apex: Acuminate, tapered. Base: Tapered. Margin: Entire. Texture and luster, upper and lower surfaces: Smooth, margins, pubescent; membranous; matte. Venation pattern: Pinnate. Color, upper surface: Close to 147A. Color, lower surface: Close to 147B.

Flower description:

*Flower type and arrangement*.—Symmetrical rosette flowers; flowers typically grown as a standard type with one terminal flower per flowering stein; flowers face upright.

*Flowering season*.—Plants of the new Rose flower year-round under greenhouse conditions; early flowering habit, plants begin flowering about 91 days after pinching.

*Flower diameter*.—About 11.2 cm.

*Flower depth* (*height*).—About 4.7 cm.

*Flower longevity*.—Excellent postproduction longevity; flowers maintain good substance for about 18 to 20 days on the plant and for about 13 to 15 days as a cut flower; flowers persistent.

*Fragrance*.—None detected.

*Flower buds*.—Length: About 5.1 cm. Diameter: About 6.3 cm. Shape: Ovoid. Texture and luster: Smooth, glabrous; matte. Color: Close to 144A.

*Petals*.—Quantity: About 35 per flower; petals imbricate. Length: About 5.4 cm. Width: About 5.8 cm. Shape: Obovate. Apex: Blunt to short acute. Base: Obtuse. Margin: Entire; slightly undulate. Texture and luster, upper and lower surfaces: Smooth, glabrous; papery to coriaceous; matte. Color: When opening, upper surface: Close to N45A. When opening, lower surface: Close to 46A. Fully opened, upper surface: Close to N45B; venation, close to N45D; color becoming closer to 53B with development. Fully opened, lower surface: Close to 46B; towards the base, close to 53C; color becoming closer to 46A with development.

*Petaloids*.—Quantity: About five in a single whorl. Length: About 3 cm. Width: About 2.1 cm. Shape: Irregularly shaped. Apex: Blunt to short acute. Base: Tapered. Margin: Mostly uneven; undulate. Texture and luster, upper and lower surfaces: Slightly rugose, glabrous; papery to coriaceous; matte. Color: When opening, upper surface: Close to N45A. When opening, lower surface: Close to 53A. Fully opened, upper surface: Close to N45A; venation, close to 45C; color becoming closer to N45B, 156D and 61D with development. Fully opened, lower surface: Close to N45A; venation, close to 45C; color becoming closer to 46A, 61C and 157A with development.

*Sepals*.—Quantity per flower: Typically five in a single whorl. Length: About 3.9 cm. Width: About 1.6 cm. Shape: Roughly deltoid. Apex: Tapered. Base: Truncate. Margin: Entire; ciliate and/or glandular. Texture and luster, upper surface: Pubescent, leathery; matte. Texture and luster, lower surface: Glabrous, leathery; matte. Color: When opening and fully opened, upper surface: Close to 143A. When opening and fully opened, lower surface: Close to 143B.

*Reproductive organs*.—Stamens: Quantity: About 184 per flower. Filament length: About 6 mm Filament color: Close to 67A and 155C. Anther size: About 2.8 mm by 1.8 cm. Anther shape: Reniform. Anther color: Close to 160A and 45C. Pollen amount: Scarce. Pollen color: Close to 162A. Pistils: Quantity: About 173 per flower. Pistil length: About 1.5 cm. Stigma diameter: About 1 mm Stigma shape: Broadly reniform. Stigma color: Close to 161C. Style length: About 1.5 cm. Style color: Close to 41D and 157A. Ovary color: Close to 157C. Receptacle height: About 1.2 cm. Receptacle diameter: About 1.5 cm. Receptacle shape: Cup-shaped. Receptacle texture: Smooth, glabrous. Receptacle color: Close to 144A. Fruits and seeds: To date, fruit and seed development have not been observed on plants of the new Rose.

Pathogen & pest tolerance: Plants of the new Rose have not been observed to be tolerant to pathogens and pests common to Rose plants.

Temperature tolerance: Plants of the new Rose have been observed to tolerate temperatures ranging from 0° C. to 35° C.

It is claimed:

1. A new and distinct Rose plant named 'ESM R325' as illustrated and described.

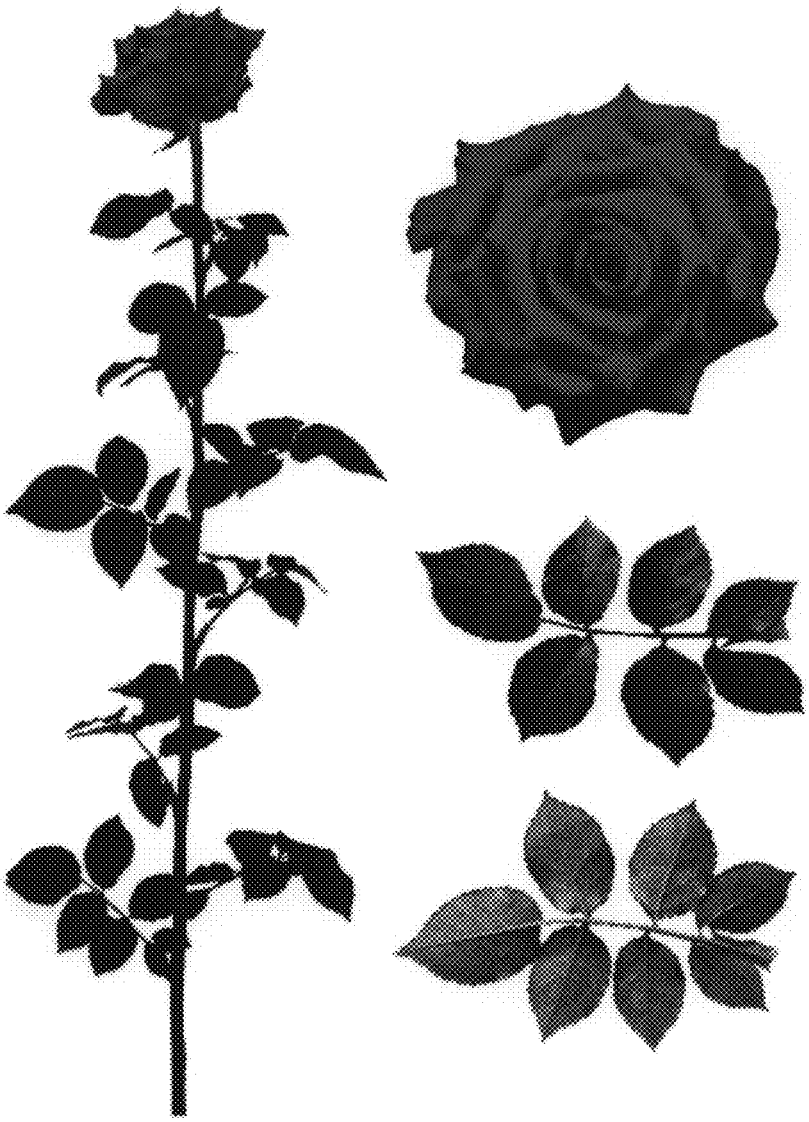

* * * * *